(12) United States Patent
Pratt

(10) Patent No.: US 11,363,238 B1
(45) Date of Patent: Jun. 14, 2022

(54) SYSTEMS AND METHODS FOR HEALTHCARE FACILITY CONTACTLESS COMMUNICATION

(71) Applicant: Healthcare Information, LLC, Loveland, OH (US)

(72) Inventor: Richard L. Pratt, Cincinnati, OH (US)

(73) Assignee: Healthcare Information, LLC, Loveland, OH (US)

( * ) Notice: Subject to any disclaimer, the term of this patent is extended or adjusted under 35 U.S.C. 154(b) by 0 days.

(21) Appl. No.: 17/475,835

(22) Filed: Sep. 15, 2021

Related U.S. Application Data

(60) Provisional application No. 63/084,269, filed on Sep. 28, 2020.

(51) Int. Cl.
*H04N 7/15* (2006.01)
*G16H 80/00* (2018.01)
*H04L 65/1076* (2022.01)

(52) U.S. Cl.
CPC .............. *H04N 7/15* (2013.01); *G16H 80/00* (2018.01); *H04L 65/1076* (2013.01)

(58) Field of Classification Search
CPC ... A61B 5/02055; A61B 5/412; A61B 5/7253; G06Q 10/10; G08B 7/066; G08B 21/02; G08B 1/08; G08B 7/005; G16H 10/60; G16H 40/67; G16H 80/00; G16H 40/20; G16H 50/30; H04L 65/1076; H04L 67/1093; H04N 7/147; H04N 7/15; H04N 7/18; H04N 21/42222; A61G 7/053; A61G 15/00

USPC .............. 348/14.08, 77, 734; 600/300, 301; 705/2, 3; 340/286.07; 601/15
See application file for complete search history.

(56) References Cited

U.S. PATENT DOCUMENTS

| | | | | |
|---|---|---|---|---|
| 8,273,018 | B1 * | 9/2012 | Fackler | G08B 7/066 600/300 |
| 2002/0186123 | A1 * | 12/2002 | Kivisto | G08B 1/08 340/286.07 |
| 2003/0139693 | A1 * | 7/2003 | Swift | A61G 15/00 601/49 |
| 2007/0056108 | A1 * | 3/2007 | Nikolopoulos | A47G 9/1054 5/636 |
| 2008/0068447 | A1 * | 3/2008 | Mattila | H04N 7/147 348/14.08 |
| 2008/0252793 | A1 * | 10/2008 | Choi | H04N 21/42222 348/E5.103 |
| 2010/0134609 | A1 * | 6/2010 | Johnson | G16H 40/67 348/143 |

(Continued)

*Primary Examiner* — Gerald Gauthier
(74) *Attorney, Agent, or Firm* — Ulmer & Berne LLP

(57) ABSTRACT

Systems and methods for managing communications within a healthcare facility are provided. An audio communication channel is provisioned between a clinician video conferencing unit and a pillow speaker. A video communication channel is provisioned between the clinician video conferencing unit and a room-mounted video conferencing unit. The pillow speaker and room-mounted video conferencing unit are both located inside a room at the healthcare facility while the clinician video conferencing unit is located outside of the room, such as in the hallway, at a nurse's station, or external to the facility. The audio communication channel and the video communication channel are concurrently maintained during a contactless video conference session.

20 Claims, 3 Drawing Sheets

(56) References Cited

U.S. PATENT DOCUMENTS

| | | | |
|---|---|---|---|
| 2011/0134339 A1* | 6/2011 | Butler | H04N 21/42222 |
| | | | 348/734 |
| 2012/0026308 A1* | 2/2012 | Johnson | H04N 7/18 |
| | | | 348/E7.085 |
| 2012/0029303 A1* | 2/2012 | Shaya | A61B 8/00 |
| | | | 600/300 |
| 2013/0300548 A1* | 11/2013 | Robinson | G16H 40/20 |
| | | | 340/286.07 |
| 2014/0168397 A1* | 6/2014 | Greco | G16H 40/67 |
| | | | 348/77 |
| 2015/0092010 A1* | 4/2015 | Liu | H04N 7/15 |
| | | | 348/14.08 |
| 2015/0119652 A1* | 4/2015 | Hyde | G16H 40/67 |
| | | | 600/301 |
| 2015/0302538 A1* | 10/2015 | Mazar | G06Q 10/10 |
| | | | 705/2 |
| 2015/0310183 A1* | 10/2015 | Madhavan | G16H 40/67 |
| | | | 705/3 |
| 2016/0302666 A1* | 10/2016 | Shaya | H04L 65/403 |
| 2017/0032093 A1* | 2/2017 | Norton | G16H 40/20 |
| 2017/0323074 A1* | 11/2017 | Chiang | H04L 63/08 |
| 2019/0108908 A1* | 4/2019 | Faulks | G16H 80/00 |
| 2019/0307405 A1* | 10/2019 | Terry | A61G 7/053 |
| 2019/0336085 A1* | 11/2019 | Kayser | A61B 5/412 |
| 2019/0357880 A1* | 11/2019 | Naidoo | G06Q 40/08 |
| 2020/0021930 A1* | 1/2020 | Iswanto | A61B 5/7253 |
| 2020/0066415 A1* | 2/2020 | Hettig | G16H 50/30 |

* cited by examiner

SYSTEMS AND METHODS FOR HEALTHCARE FACILITY CONTACTLESS COMMUNICATION

CROSS-REFERENCE TO RELATED APPLICATIONS

This application claims the benefit of U.S. Patent Application Ser. No. 63/084,269, filed Sep. 28, 2020, and entitled SYSTEMS AND METHODS FOR HEALTHCARE FACILITY CONTACTLESS COMMUNICATION, the disclosure of which is incorporated herein by reference in its entirety.

BACKGROUND

Healthcare facilities, such as hospitals, rehabilitation centers, are finding increasing need to respond to increased occupancy and other issues associated with infectious disease outbreaks. As the desire to communicate with certain patients in a contactless manner may be increasing, the ability for clinicians to effectively communicate with such patients in a contactless manner is limited.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
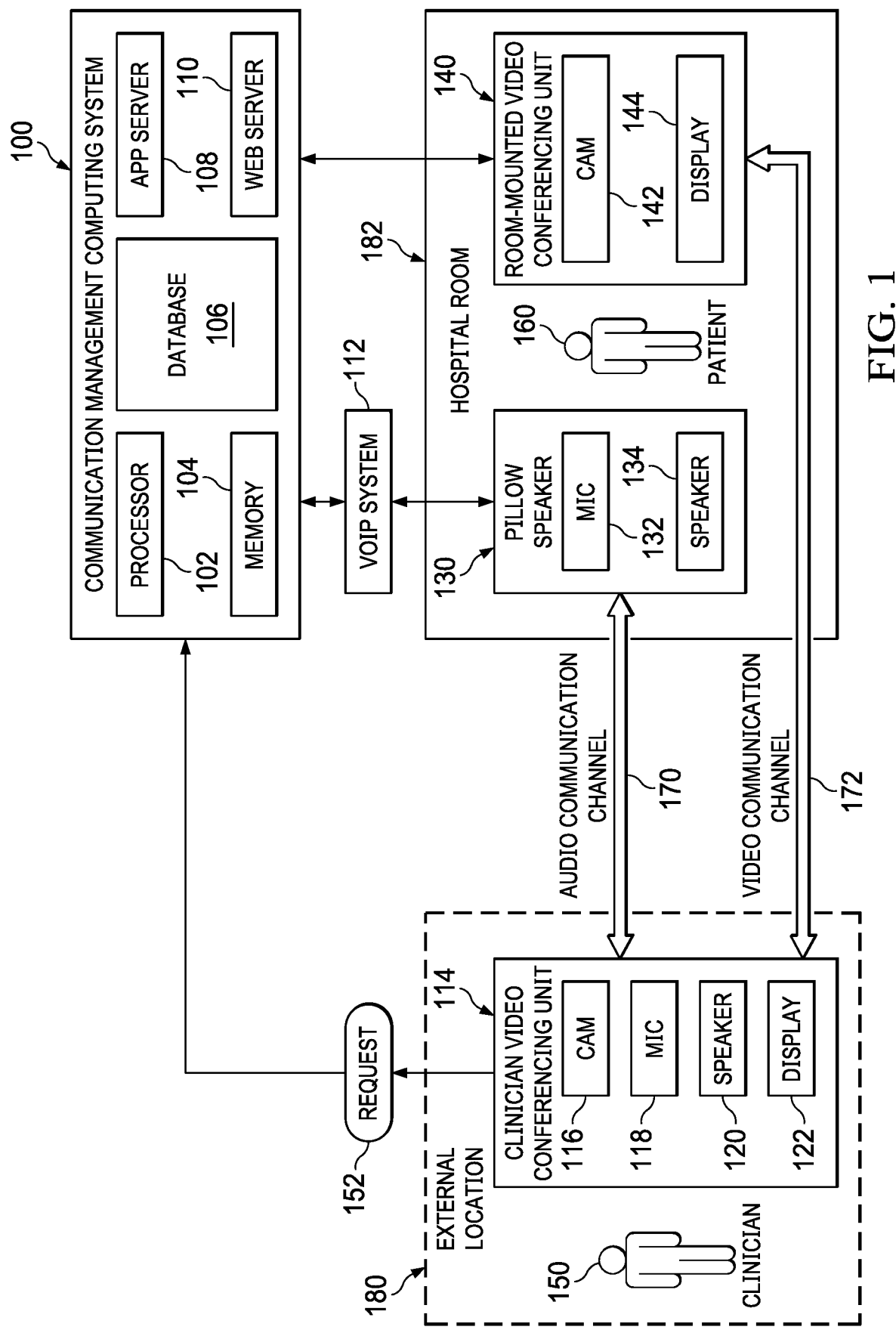
FIG. 1 depicts a communication management computing system in communication with an audio communication channel and a video communication channel between a clinician and a patient in accordance with one non-limiting embodiment.

Various non-limiting embodiments of the present disclosure will now be described to provide an overall understanding of the principles of the structure, function, and use of systems, apparatuses, devices, and methods disclosed. One or more examples of these non-limiting embodiments are illustrated in the selected examples disclosed and described in detail with reference made to FIGS. 1-3 in the accompanying drawings. Those of ordinary skill in the art will understand that systems, apparatuses, devices, and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems, apparatuses, devices, and methods disclosed herein are described in detail by way of examples and with reference to the figures. The examples discussed herein are examples only and are provided to assist in the explanation of the apparatuses, devices, systems and methods described herein. None of the features or components shown in the drawings or discussed below should be taken as mandatory for any specific implementation of any of these apparatuses, devices, systems or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identification of specific details or examples is not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented, but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and include a wide variety of electronic information, including executable code; content such as text, video data, and audio data, among others; and various codes or flags. The terms "information," "data," and "content" are sometimes used interchangeably when permitted by context. It should be noted that, although for clarity and to aid in understanding, some examples discussed herein might describe specific features or functions as part of a specific component or module, or as occurring at a specific layer of a computing device (for example, a hardware layer, operating system layer, or application layer), those features or functions may be implemented as part of a different component or module or operated at a different layer of a communication protocol stack. Those of ordinary skill in the art will recognize that the systems, apparatuses, devices, and methods described herein can be applied to, or easily modified for use with, other types of equipment, can use other arrangements of computing systems, and can use other protocols, or operate at other layers in communication protocol stacks, than are described.

As described in more detail below, the present disclosure generally relates to the management of communications within a healthcare facility. The systems and methods described herein can be used in a wide variety of operational contexts. Thus, while certain examples are described in the context of a hospital having hospital rooms, this disclosure is not so limited. Instead, the systems and methods in accordance with the present disclosure can be used in a wide variety of healthcare facilities, such as rehabilitation centers, outpatient facilities, surgical centers, urgent care centers, community health clinics, among numerous others.

Referring now to FIG. 1, one example embodiment of the present disclosure can comprise a communication management computing system 100. The communication management computing system 100 can be provided using any suitable processor-based device or system, such as a personal computer, laptop, server, mainframe, or a collection (e.g., network) of multiple computers, for example. The communication management computing system 100 can be locally provided at a healthcare facility, although this disclosure is not so limited. For instance, the communication management computing system 100, or components therefor, can be a cloud-based service accessible through network communications. In any event, the communication management computing system 100 can include one or more processors 102 and one or more computer memory units 104. For convenience, only one processor 102 and only one memory unit 104 are shown in FIG. 1. The processor 102 can execute software instructions stored on the memory unit 104. The processor 102 can be implemented as an integrated circuit (IC) having one or multiple cores. The memory unit 104 can include volatile and/or non-volatile memory units. Volatile memory units can include random access memory (RAM), for example. Non-volatile memory units can include read only memory (ROM), for example, as well as mechanical non-volatile memory systems, such as, for example, a hard disk drive, an optical disk drive, etc. The RAM and/or ROM memory units can be implemented as discrete memory ICs, for example.

The memory unit 104 can store executable software and data for the communication management computing system 100. When the processor 102 of the communication management computing system 100 executes the software, the processor 102 can be caused to perform the various operations of the communication management computing system 100. Data used by the communication management computing system 100 can be from various sources, such as a database(s) 106, which can be an electronic computer database, for example. The data stored in the database(s) 106 can be stored in a non-volatile computer memory, such as a hard disk drive, a read only memory (e.g., a ROM IC), or other types of non-volatile memory. In some embodiments, one or more databases 106 can be stored on a remote electronic computer system, for example. As is to be appreciated, a variety of other databases, or other types of memory storage structures, can be utilized or otherwise associated with the communication management computing system 100.

The communication management computing system 100 can also be in communication with a plurality of computing devices in a healthcare facility, such as a clinician video conferencing unit 114 and a room-mounted video conferencing unit 140. The room-mounted video conferencing unit 140 can be mounted, or otherwise positioned, in a hospital room 182. The clinician video conferencing unit 114 can be mounted, for example, in location 180 that is external to the hospital room 182. By way of example, the clinician video conferencing unit 114 can be mounted in a hallway external to the hospital room 182. The clinician video conferencing unit 114 can alternatively be mounted or positioned, for example, at a nurse's station or other location internal or external to the healthcare facility. Moreover, as discussed in detail below, in some embodiments multiple clinician video conferencing units 114 and multiple room-mounted video conferencing units 140 can be in communication with the communication management computing system 100. As used herein, the term "clinician" is not to be limiting to any particular type of caregiver, but instead is to broadly refer any type of hospital staff, doctor, nurse, nurse practitioner, administrator, physical therapist, and so forth.

A pillow speaker 130 can also be positioned in the hospital room 182. The pillow speaker 130 is typically a plastic box with a cord extending therefrom to be plugged into a wall receptacle. The pillow speaker 130 also usually includes one or more buttons to turn an in-room television on and off, control channel selection, and control volume. Some types of pillow speakers 130 can also include a nurse call button and a microphone 132. Communications between the pillow speaker 130 and the nurse's station can be managed by, for example, a voice over IP (VOIP) system 112. The pillow speaker 130 can include an audio speaker 134 which provides audio to a patient 160. The pillow speaker 130 usually is set on the mattress within easy reach of the patient 160, or may dangle from a railing of the bed frame near the patient 160.

The clinician video conferencing unit 114 can have various components that facilitate video conferencing, such as, for example, a camera 116, a microphone 118, and an audio speaker 120. In some embodiments, the clinician video conferencing unit 114 can also have a display 122. The room-mounted video conferencing unit 140 can include, for example, a camera 142 and a display 144. Unlike the pillow speaker 130, the room-mounted video conferencing unit 140 does not need to be positioned in a location that is physically within close proximity to the patient 160. Instead, the room-mounted video conferencing unit 140 can be positioned at a wall opposite of the hospital bed, for example. As such, the patient 160 lying or sitting in the bed is in a field of view of the camera 142 of the room-mounted video conferencing unit 140.

The clinician video conferencing unit 114 and the room-mounted video conferencing unit 140 can each be any type of computer device suitable for communication with the communication management computing system 100, such as a tablet computer, for example. The clinician video conferencing unit 114 and the room-mounted video conferencing unit 140 can comprise various software programs such as system programs and applications to provide computing capabilities in accordance with the described embodiments. System programs can include, without limitation, an operating system (OS), device drivers, programming tools, utility programs, software libraries, application programming interfaces (APIs), and so forth. Exemplary operating systems can include, for example, PALM OS, MICROSOFT OS, APPLE OS, ANDROID OS, UNIX OS, LINUX OS, SYMBIAN OS, EMBEDIX OS, Binary Run-time Environment for Wireless (BREW) OS, JavaOS, a Wireless Application Protocol (WAP) OS, and others.

As shown in FIG. 1, the communication management computing system 100 can include several computer servers and databases. For example, the communication management computing system 100 can include one or more application servers 108, web servers 110, and/or any other type of servers. For convenience, only one application server 108 and one web server 110 are shown in FIG. 1, although it should be recognized that the disclosure is not so limited. The servers can cause content to be sent to the clinician video conferencing unit 114 and/or the room-mounted video conferencing unit 140. The servers 108 and 110 can comprise processors (e.g., CPUs), memory units (e.g., RAM, ROM), non-volatile storage systems (e.g., hard disk drive systems), etc. The servers 108 and 110 can utilize operating systems, such as Solaris, Linux, or Windows Server operating systems, for example.

The web server 110 can provide a graphical web user interface through which various users of the system can interact with the communication management computing system 100. The web server 110 can accept requests, such as HTTP requests, from clients, and serve the clients responses, such as HTTP responses, along with optional data content, such as web pages (e.g., HTML documents) and linked objects (such as images, video, and so forth). The application server 108 can provide a user interface for users who do not communicate with the communication management computing system 100 using a web browser. The clinician video conferencing unit 114 and the room-mounted video conferencing unit 140 can have special software installed that allows them to communicate with the application server 108 via the network.

Embodiments of the communication management computing system 100 can also be implemented in cloud computing environments. "Cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The system depicted in FIG. 1 can beneficially facilitate contactless interaction between a clinician 150 and the patient 160 without the patient 160 having to necessarily take any physical action. For example, the clinician 150 can approach the clinician video conferencing unit 114, as may be mounted external to the hospital room 182, for example. Through interactions with the clinician video conferencing unit 114, such as via a touch screen interface, for example, a request 152 for a video conference can be sent to and received by the communication management computing system 100. Upon receiving the request, the communication management computing system 100 can communicate with the VOIP system 112 to provision an audio communication channel 170 between the pillow speaker 130 and the clinician video conferencing unit 114. In this regard, the clinician 150 is able to speak to the patient 160 through the pillow speaker 130 without requiring the patient 160 to take any physical action. In some situations, the clinician 150 can ask permission from the patient 160 via oral communications to commence a video conference. As is to be appreciated, however, in other situations, the patient 160 may not be able to orally communicate with the clinician 150. In any event, once the clinician 150 wishes to commence a video conference, the clinician 150 can interact with the clinician video conferencing unit 114 to send another request 152 to the communication management computing system 100, which requests a video feed from the room-mounted video conferencing unit within the hospital room 182.

The communication management computing system 100 can then provision a video communication channel 172 between the camera 142 of the room-mounted video conferencing unit 140 and the clinician video conferencing unit 114 for real-time video display of the patient 160 to the clinician 150 on the clinician video conferencing unit 114. In some embodiments, a video feed of the clinician 150 is provided to the room-mounted video conferencing unit 140 for display to the patient 160. As illustrated in FIG. 1, the audio communication channel 170 between the clinician video conferencing unit 114 and the pillow speaker 130 and the video communication channel 172 between the clinician video conferencing unit 114 and the room-mounted video conferencing unit 140 can be concurrently maintained by the communication management computing system 100.

Figure 2:
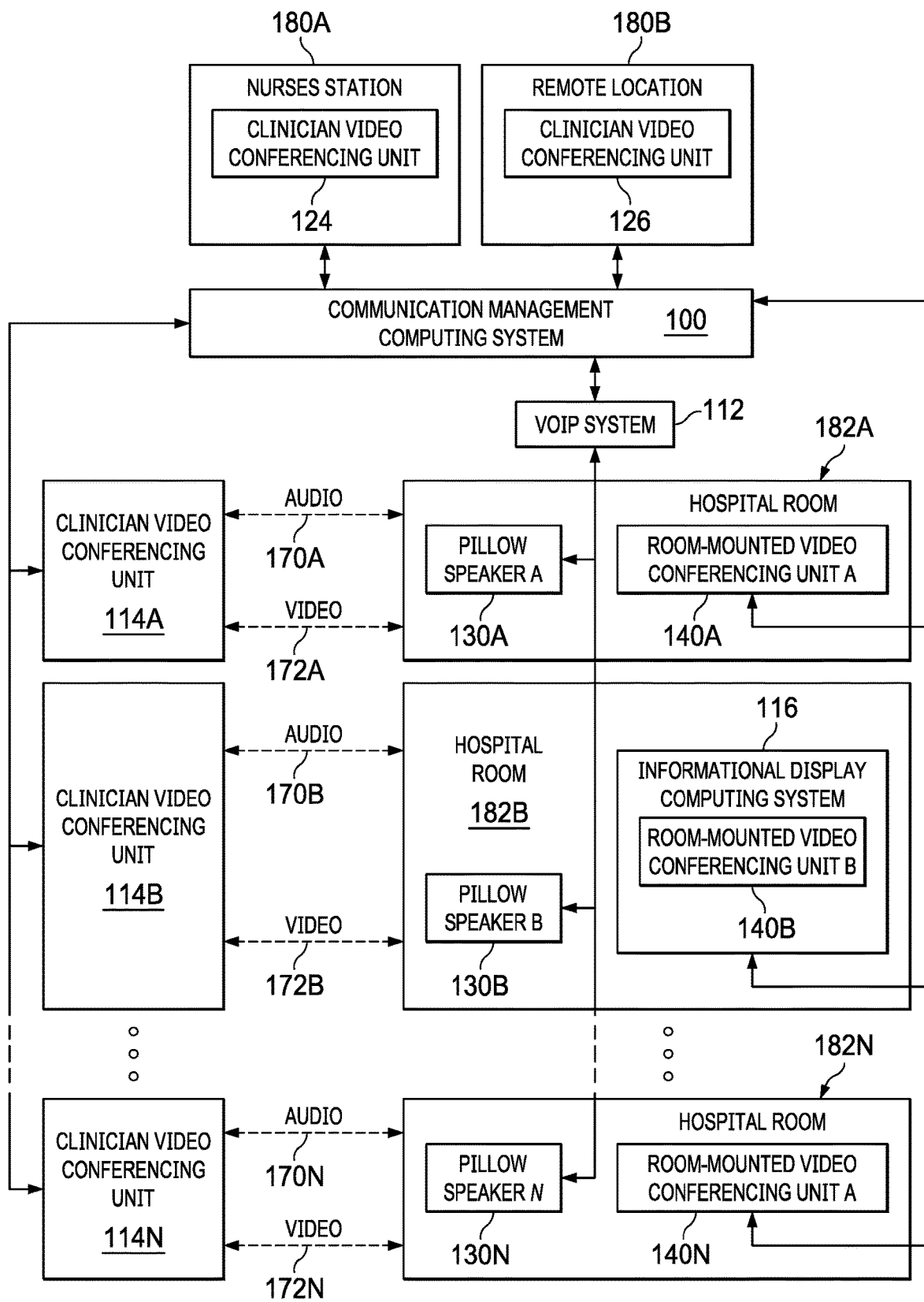
FIG. 2 depicts a communication management computing system in communication with a plurality of clinician video conferencing units, pillow speakers, and room-mounted video conferencing units in accordance with one non-limiting embodiment.

While FIG. 1 depicts the communication management computing system 100 in communication with one clinician video conferencing unit 114 and one room-mounted video conferencing unit 140 for illustration purposes, this disclosure is not so limited. In fact, as healthcare facilities have numerous hospital rooms, communication management computing systems in accordance with the present disclosure can be in communication with a plurality of clinician video conferencing units and a plurality of room-mounted video conferencing units. FIG. 2 depicts the communication management computing system 100 in communication with a plurality of clinician video conferencing units 114A-N, a plurality of pillow speakers 130A-N, and a plurality of room-mounted video conferencing units 140A-N in accordance with one non-limiting embodiment. As shown in FIG. 2, the communication management computing system 100 can facilitate the concurrent provisioning of audio communication channels 170A-N and video communication channels 172A-N between the various clinician video conferencing units 114A-N and the various hospital rooms 182A-N.

While the plurality of clinician video conferencing units 114A-N may be mounted in a hallway outside of the respective hospital rooms 182A-N, FIG. 2 further illustrates other example locations of various clinician video conferencing units. For instance, a clinician video conferencing unit 124 is shown positioned at a nurse's station 180A, or other suitable position within a healthcare facility. Through this clinician video conferencing unit 124, a clinician can select the hospital room 182A-N with which to initiate a contactless video conference session.

In some embodiments, a clinician video conferencing unit 126, which is positioned at a location 180B, can communicate with the communication management computing system. The location 180B can be physically external to the healthcare facility in which the hospital rooms 182A-N are located. The location 180B can be, for example, a physician's office, the home of a patient's family member, another healthcare facility, and so forth.

FIG. 2 also illustrates that one or more of the room-mounted video conferencing units 140A-N can be a component of other equipment that is positioned in the hospital room. Referring to room-mounted video conferencing unit 140B, for example, this unit is shown incorporated into an informational display computing system 116 that is positioned in the hospital room 182B.

Figure 3:
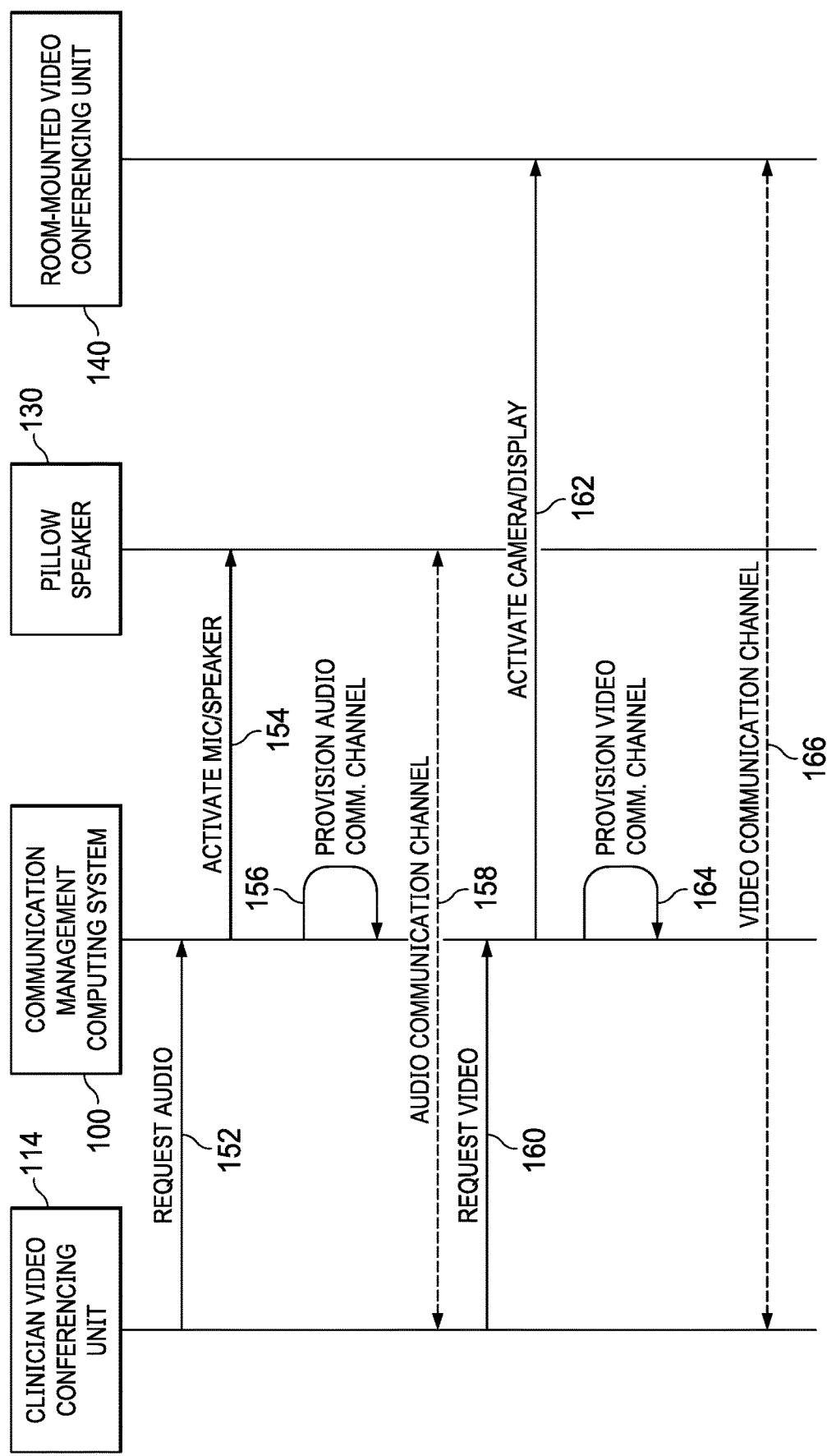
FIG. 3 depicts a message sequent chart in accordance with one non-limiting embodiment.

FIG. 3 depicts an example message sequent chart in accordance with one non-limiting embodiment. At 152, a request for audio is sent from the clinician video conferencing unit 114 and received by the communication management computing system 100. In particular, the request 152 can request the provisioning of an audio communication channel between the clinician video conferencing unit 114 and a particular room-mounted video conferencing unit, shown in FIG. 3 as room-mounted video conferencing unit 140. Upon receiving the request 152, the communication management computing system 100, at 154, can cause the activation of the microphone and speaker on the pillow speaker 130 to provision an audio communication channel 156. As is to be appreciated, the communication management computing system 100 can utilize a VOIP system to activate the pillow speaker 130. An operator of the clinician video conferencing unit 114 and the patient proximate to the pillow speaker 130 can then engage in verbal communications via an audio communication channel 158.

At 160, a request for video is sent from the clinician video conferencing unit 114 and received by the communication management computing system 100. Responsive to receiving the request 160, at 162, the communication management computing system 100 can cause the activation of the camera and display on the room-mounted video conferencing unit 140. At 164, the communication management computing system 100 can provision a video communication channel between the clinician video conferencing unit 114 and the room-mounted video conferencing unit 140. As depicted in FIG. 3, a video communication channel 166 can then allow for video communications between the clinician video conferencing unit 114 and the room-mounted video conferencing unit 140 via the video communication channel 166.

While FIG. 3 depicts a sequential provisioning of the audio communication channel 158 and the video communication channel 166, this disclosure is not so limited. For example, in some embodiments, the communication management computing system 100 can provision each of the audio communication channel 158 and the video communication channel 166 substantially at the same time. Nevertheless, the audio communication channel 158 will be established between the clinician video conferencing unit 114 and the pillow speaker 130 and the video communication channel 166 will be established between the room-mounted video conferencing unit 140 and the clinician video conferencing unit 114.

The foregoing description of embodiments and examples has been presented for purposes of description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent articles by those of ordinary skill in the art. Rather it is hereby intended the scope be defined by the claims appended hereto.

What is claimed is:

1. A method for clinician and patient contactless communication, comprising:
   receiving, by a communication management computing system from a clinician video conferencing unit, a request for a video conference, wherein the clinician video conferencing unit is positioned external of a hospital room of a patient, wherein a pillow speaker is positioned within the hospital room at a first location, wherein a room-mounted video conferencing unit is separate from the pillow speaker and positioned within the hospital room at a second location, wherein the pillow speaker comprises a microphone and a speaker, and wherein the room-mounted video conferencing unit comprises a video camera;
   provisioning, by the communication management computing system, an audio communication channel between the clinician video conferencing unit and the pillow speaker;
   subsequent to provisioning the audio communication channel between the clinician video conferencing unit and the pillow speaker, receiving, by the communication management computing system from the clinician video conferencing unit, a request for a video feed from the room-mounted video conferencing unit;
   provisioning, by the communication management computing system, a video communication channel between the video camera of the room-mounted video conferencing unit and the clinician video conferencing unit for real-time video display of the patient to the clinician on the clinician video conferencing unit; and
   concurrently maintaining, by the communication management computing system, the audio communication channel between the clinician video conferencing unit and the pillow speaker and the video communication channel between the clinician video conferencing unit and the room-mounted video conferencing unit.

2. The method of claim 1, wherein the clinician video conferencing unit is positioned in a hallway proximate to an entrance of the hospital room.

3. The method of claim 1, wherein the clinician video conferencing unit is positioned at a nurse's station.

4. The method of claim 1, wherein the hospital room is within a health facility and the clinician video conferencing unit is positioned external of the health facility.

5. The method of claim 1, wherein the clinician video conferencing unit comprises a video camera, and the method further comprises:
   provisioning, by the communication management computing system, a video feed from the video camera of the clinician video conferencing unit to the room-mounted video conferencing unit for real-time video display of the clinician to the patient on the room-mounted video conferencing unit.

6. The method of claim 5, further comprising:
   activating, by the communication management computing system, the video camera of the room-mounted video conferencing unit and the video camera of the clinician video conferencing unit responsive to receiving the request for the video feed from the room-mounted video conferencing unit.

7. The method of claim 1, wherein provisioning the audio communication channel between the clinician video conferencing unit and the pillow speaker comprises activating the microphone and the speaker of the pillow speaker without patient interaction.

8. The method of claim 1, wherein the room-mounted video conferencing unit is a component of an in-room informational display computing system.

9. A healthcare video conferencing system, comprising:
   a clinician video conferencing unit comprising a microphone, a speaker, a video camera, and a display screen, wherein the clinician video conferencing unit is positioned external to a hospital room;

a room-mounted video conferencing unit comprising a video camera and a display screen, wherein the room-mounted video conferencing unit is positioned at a first location within the hospital room;

a pillow speaker comprising a microphone and a speaker, wherein the pillow speaker is separate from the room-mounted video conferencing unit and is positioned within the hospital room at a second location;

a communication management computing system comprising a memory and a processor, wherein the memory stores instructions which when executed cause the processor to:

provide an audio communication channel between the clinician video conferencing unit and the pillow speaker; and subsequent to providing the audio communication channel between the clinician video conferencing unit and the pillow speaker, providing a video communication channel between the clinician video conferencing unit and the room-mounted video conferencing unit.

10. The healthcare video conferencing system of claim 9, wherein the clinician video conferencing unit is positioned in a hallway proximate to an entrance of the hospital room.

11. The healthcare video conferencing system of claim 9, wherein the clinician video conferencing unit is a positioned at a nurse's station.

12. The healthcare video conferencing system of claim 9, wherein the hospital room is within a health facility, and the clinician video conferencing unit is positioned external of the health facility.

13. The healthcare video conferencing system of claim 9, wherein the audio communication channel between the clinician video conferencing unit and the pillow speaker is provided without patient interaction.

14. The healthcare video conferencing system of claim 9, wherein audio from the patient is collected from the microphone of the pillow speaker and provided to the clinician video conferencing unit by the communication management computing system and wherein video of the patient is collected from the video camera of the room-mounted video conferencing unit and provided to the clinician video conferencing unit by the communication management computing system.

15. The healthcare video conferencing system of claim 14, wherein audio from the clinician is collected from the microphone of the clinician video conferencing unit and provided to the speaker of the pillow speaker by the communication management computing system and wherein video of the clinician is collected from the video camera the clinician video conferencing unit and provided to the room-mounted video conferencing unit by the communication management computing system.

16. The healthcare video conferencing system of claim 15, further comprising a tablet computing device, wherein the room-mounted video conferencing unit is a component of the tablet computing device.

17. A method for clinician and patient contactless communication, comprising:

receiving a request for a video conference from a clinician video conferencing unit, wherein the clinician video conferencing unit is positioned external of a hospital room of a patient, wherein a pillow speaker is positioned within the hospital room at a first location, wherein a room-mounted video conferencing unit is separate from the pillow speaker and positioned within the hospital room at a second location, wherein the pillow speaker comprises a microphone and a speaker, and wherein the room-mounted video conferencing unit comprises a video camera;

provisioning an audio communication channel between the clinician video conferencing unit and the pillow speaker;

provisioning a video communication channel between the video camera of the room-mounted video conferencing unit and the clinician video conferencing unit for real-time video display of the patient to the clinician on the clinician video conferencing unit; and concurrently maintaining the audio communication channel between the clinician video conferencing unit and the pillow speaker and the video communication channel between the clinician video conferencing unit and the room-mounted video conferencing unit.

18. The method of claim 17, wherein the clinician video conferencing unit is positioned either in a hallway proximate to an entrance of the hospital room or at a nurse's station.

19. The method of claim 17, wherein the hospital room is within a health facility and the clinician video conferencing unit is positioned external of the health facility.

20. The method of claim 17, wherein the clinician video conferencing unit comprises a video camera, and the method further comprises:

provisioning a video feed from the video camera of the clinician video conferencing unit to the room-mounted video conferencing unit for real-time video display of the clinician to the patient on the room-mounted video conferencing unit.

* * * * *